(12) United States Patent
Nakata et al.

(10) Patent No.: US 8,102,524 B2
(45) Date of Patent: Jan. 24, 2012

(54) DEGREE-OF-DISPERSION DETERMINATION METHOD FOR SINGLE-WALLED CARBON NANOTUBES AND DEGREE-OF-DISPERSION DETERMINATION APPARATUS FOR SINGLE-WALLED CARBON NANOTUBES

(75) Inventors: Yasushi Nakata, Kyoto (JP); Hiroshi Uchihara, Kyoto (JP)

(73) Assignee: Horiba, Ltd., Kyoto (JP)

( * ) Notice: Subject to any disclaimer, the term of this patent is extended or adjusted under 35 U.S.C. 154(b) by 374 days.

(21) Appl. No.: 12/398,934

(22) Filed: Mar. 5, 2009

(65) Prior Publication Data

US 2010/0110421 A1    May 6, 2010

(30) Foreign Application Priority Data

Oct. 30, 2008    (JP) .................................. 2008-280259

(51) Int. Cl.
*G01J 3/44*    (2006.01)
(52) U.S. Cl. ....................................................... 356/301
(58) Field of Classification Search .................... 356/301
See application file for complete search history.

(56) References Cited

U.S. PATENT DOCUMENTS

2006/0036018 A1*    2/2006    Winey et al. .................. 524/496

FOREIGN PATENT DOCUMENTS

| JP | 2007-070224 | 3/2007 |
| JP | 2007-197304 | 8/2007 |
| JP | 2007-320828 | 12/2007 |

OTHER PUBLICATIONS

Heller et al. "Using Raman spectroscopy to elucidate the aggregation state of single-walled carbon nanotubes", 2004, J Phys Chem B, 108, pp. 6905-6909.*
Rasheed et al. "Improving dispersion of single-walled carbon nanotubes in a polymer matrix using specific interactions", 2006, American Chemical Society, 18, pp. 3513-3522.*
Yoon et al. "The quantitative characterization of the dispersion state of single-walled carbon nanotubes using Raman spectroscopy and atomic force microscopy", Jun. 28, 2008, Elsevier, pp. 1530-1534.*
Nakata, Yasushi; "Characterization of CMC-Wrapped Carbon Nanotubes in The Spin-Coated Thin-Film By Resonance Raman Spectroscopy"; Pittsburg Conference on Analytical Chemistry and Applied Spectroscopy, 2008; 2 pages.

* cited by examiner

*Primary Examiner* — Kara E Geisel

(57) ABSTRACT

Laser light having an energy of 1.9±0.1 eV is projected onto a carbon nanotube-containing substance so that a Raman spectrum is acquired. On the basis of the intensity of a peak at Raman shift 221±5 cm$^{-1}$ caused by aggregates of single-walled carbon nanotubes, the degree of dispersion of single-walled carbon nanotubes in the carbon nanotube-containing substance is determined. A lower intensity of the peak indicates a higher degree of dispersion in the carbon nanotube-containing substance. As such, when the intensity of a particular peak contained in a Raman spectrum is measured, the degree of dispersion of single-walled carbon nanotubes in a carbon nanotube-containing substance can be evaluated easily and clearly.

8 Claims, 12 Drawing Sheets

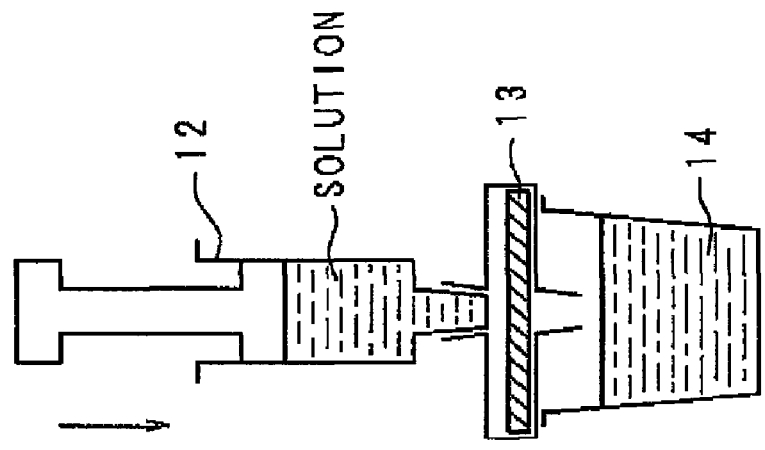
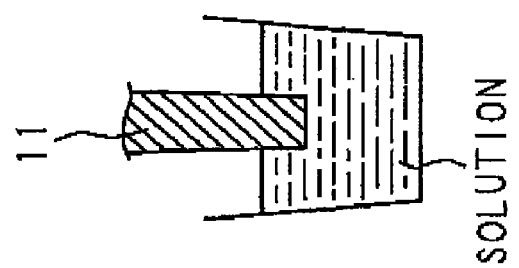
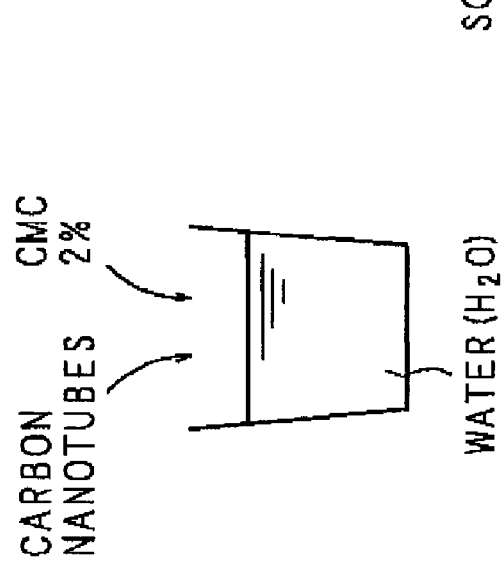

F I G. 4
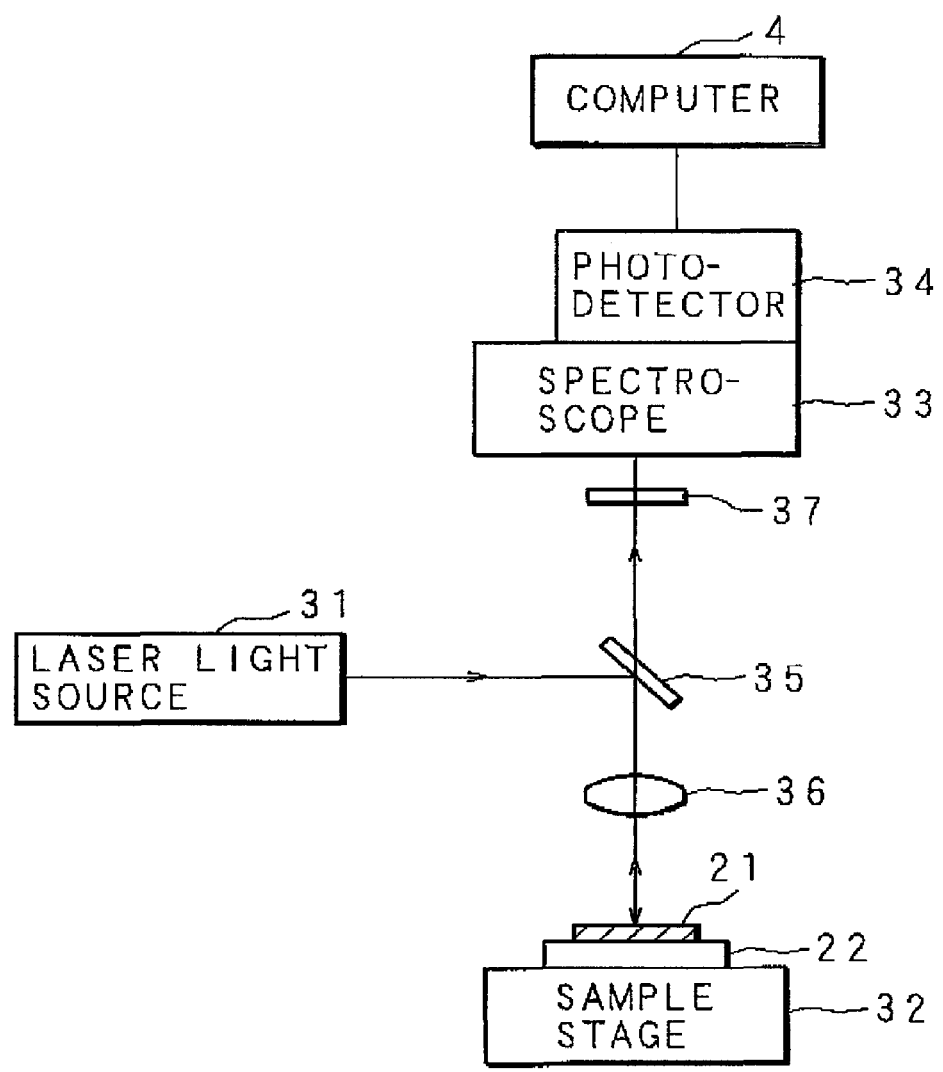

F I G. 8
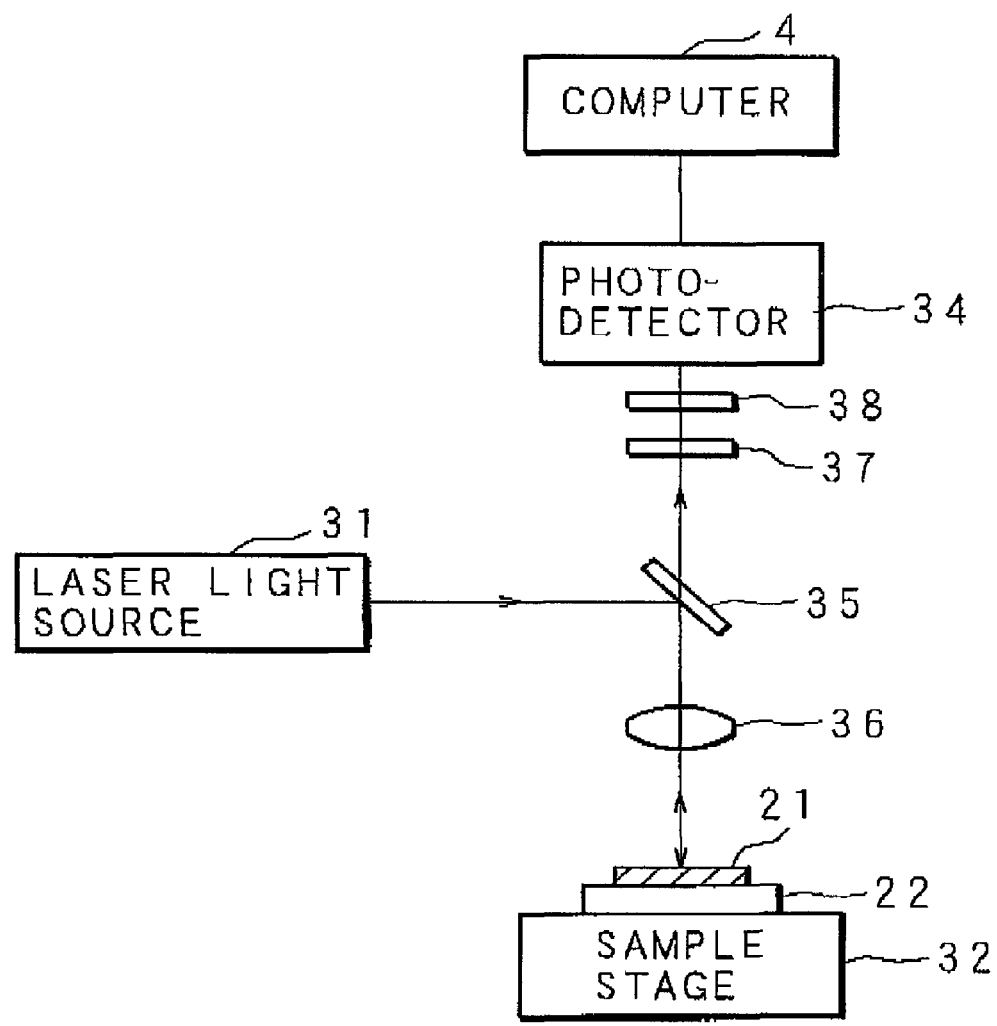

DEGREE-OF-DISPERSION DETERMINATION METHOD FOR SINGLE-WALLED CARBON NANOTUBES AND DEGREE-OF-DISPERSION DETERMINATION APPARATUS FOR SINGLE-WALLED CARBON NANOTUBES

CROSS-REFERENCE TO RELATED APPLICATIONS

This non-provisional application claims priority under 35 U.S.C. §119(a) on Patent Application No. 2008-280259 filed in Japan on Oct. 30, 2008, the entire contents of which are hereby incorporated by reference.

FIELD

The present invention relates to: a method of determining the degree of dispersion corresponding to the ratio of single-walled carbon nanotubes that do not form aggregates and are in an isolated state within single-walled carbon nanotubes contained in a carbon nanotube-containing substance; and a degree-of-dispersion determination apparatus for single-walled carbon nanotubes.

BACKGROUND

The carbon nanotube (CNT) is a substance formed when a large number of six-membered rings composed of carbon atoms are linked together into a tubular shape. An ordinary carbon nanotube has a closed structure formed together with contained five-membered rings. Further, carbon nanotubes are divided into two classes including: a multi-walled carbon nanotube (MWCNT) in which a plurality of layers each formed by linked carbon atoms are stacked; and a single-walled carbon nanotube (SWCNT) farmed in the shape of a monolayer tube.

In the prior art, a method of preparing a film sample of a carbon nanotube-containing substance is known in which solution of carbon nanotubes solubilized using surfactant is prepared and then the prepared solution is dripped onto a plate and then dried up. Patent Document 1 discloses a technique of preparing a film sample of a carbon nanotube-containing substance in which single-walled carbon nanotubes are dispersed by using carboxymethylcellulose (CMC) as surfactant. The characteristics of carbon nanotube-containing substances can be investigated by using film samples prepared as described here.

[Patent Document 1] Japanese Patent Application Laid-Open No. 2007-320828

In preparing a carbon nanotube-containing substance, it is difficult to disperse single-walled carbon nanotubes completely. Further, single-walled carbon nanotubes having been dispersed once can aggregate again so as to form aggregates. Thus, the degree of dispersion corresponding to a ratio of single-walled carbon nanotubes that do not form aggregates and are in an isolated state within single-walled carbon nanotubes contained in a carbon nanotube-containing substance having been prepared can have various values depending on the carbon nanotube-containing substance. Aggregates of single-walled carbon nanotubes do not generate photoluminescence. Thus, when a carbon nanotube-containing substance is to be used as a luminescence material, the degree of dispersion of single-walled carbon nanotubes affects the quality of the luminescence material. Accordingly, evaluation is necessary on the degree of dispersion of single-walled carbon nanotubes in a carbon nanotube-containing substance. The width of a peak or the like observed by photoluminescence spectrometry or absorption spectrophotometry of a carbon nanotube-containing substance corresponds to the degree of dispersion. Nevertheless, since the peak shape can vary also owing to factors other than the degree of dispersion, clear evaluation of the degree of dispersion has been difficult.

SUMMARY

Accordingly, it is an object of the embodiment to provide: a method of clearly determining the degree of dispersion of single-walled carbon nanotubes in a carbon nanotube-containing substance; and a degree-of-dispersion determination apparatus for single-walled carbon nanotubes.

According to an aspect of the embodiment, in a method of determining a degree of dispersion corresponding to a ratio of single-walled carbon nanotubes that do not form aggregates and are in an isolated state within single-walled carbon nanotubes contained in a carbon nanotube-containing substance, the method includes: detecting Raman scattering light generated by projecting monochromatic light into a carbon nanotube-containing substance; measuring an intensity of the Raman scattering light corresponding to a predetermined Raman shift corresponding to the monochromatic light; and on the basis of the measured intensity of the Raman scattering light, determining a degree of dispersion of the single-walled carbon nanotubes in the carbon nanotube-containing substance.

Additional objects and advantages of the embodiment will be set forth in part in the description which follows, and in part will be obvious from the description, or may be learned by practice of the invention. The object and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF DRAWINGS

FIGS. 2A, 2B and 2C are conceptual diagrams showing an example of a method of preparing carbon nanotube solution that contains single-walled carbon nanotubes.

FIG. 4 is a schematic diagram showing a structure of a Raman spectrometer according to Embodiment 1.

FIG. 8 is a schematic diagram showing a structure of a Raman spectrometer according to Embodiment 2.

DESCRIPTION OF EMBODIMENTS

Embodiment 1

Figure 1A:
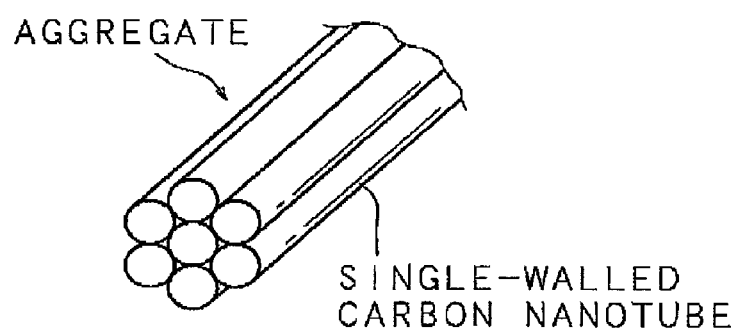
FIGS. 1A and 1B are schematic diagrams showing single-walled carbon nanotubes.
Figure 1B:
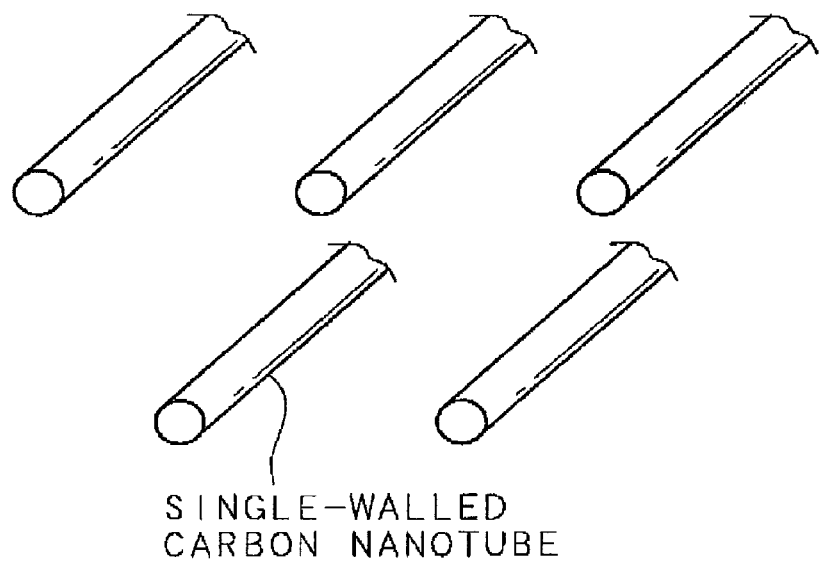

FIGS. 1A and 1B are schematic diagrams showing single-walled carbon nanotubes. Commercially available carbon nanotubes are composed of aggregates of a plurality of single-walled carbon nanotubes that aggregate with each other. FIG. 1A shows an aggregate of single-walled carbon nanotubes. A plurality of single-walled carbon nanotubes aggregate in the shape of a bundle so as to form an aggregate. FIG. 1B shows a situation that individual single-walled carbon nanotubes separate from the aggregate so that the isolated single-walled carbon nanotubes are in a dispersed state. It is known that isolated single-walled carbon nanotubes generate photoluminescence in the near infrared range. Thus, attention is focused on the possibility of application as a luminescence material. On the other hand, it is also known that aggregates of a plurality of single-walled carbon nanotubes having aggregated with each other as shown in FIG. 1A do not generate photoluminescence. Accordingly, in the development of a luminescence material composed of carbon nanotubes, a carbon nanotube-containing substance need be prepared in which individual single-walled carbon nanotubes are in a dispersed state. Then, the characteristics of the prepared carbon nanotube-containing substance need be investigated.

In the present embodiment, Raman scattering light from a carbon nanotube-containing substance that contains single-walled carbon nanotubes is measured with a Raman spectrometer. Then, on the basis of the measurement result, the degree of dispersion of the single-walled carbon nanotubes in the carbon nanotube-containing substance is determined.

FIGS. 2A, 2B and 2C are conceptual diagrams showing an example of a method of preparing a carbon nanotube solution that contains single-walled carbon nanotubes. First, as shown in FIG. 2A, approximately 2% by weight of carboxymethylcellulose (CMC) and carbon nanotubes containing single-walled carbon nanotubes are supplied into water (H2O) serving as solvent. Then, mixing and stirring are performed so that solution containing carbon nanotubes is prepared. The CMC is a chain polymer that has a large number of hydrophilic groups and hydrophobic groups. Then, a plurality of hydrophobic groups enclose a carbon nanotube so that the carbon nanotube is solubilized into water.

Then, as shown in FIG. 2B, ultrasonic waves are supplied into the solution by using an ultrasonic oscillator 11 so that single-walled carbon nanotubes are dispersed in the solution. The original carbon nanotubes contain a large amount of aggregates of a plurality of single-walled carbon nanotubes that aggregate with each other. The vibrations of the ultrasonic waves cause the individual single-walled carbon nanotubes to separate from the aggregates. Then, the separated single-walled carbon nanotubes are solubilized by the CMC so that the isolated single-walled carbon nanotubes are dispersed in the solution.

Then, as shown in FIG. 2C, the prepared solution is charged into a syringe 12. Then, the solution extruded from the syringe 12 is caused to pass through a filter 13, so that carbon nanotube solution 14 having been filtered with the filter 13 is prepared. The pore diameter of the filter 13 is set to be a size that allows the solubilized single-walled carbon nanotubes to pass through and that does not allow the aggregates of single-walled carbon nanotubes and the multi-walled carbon nanotubes to pass through easily. For example, the pore diameter of the filter 13 is 0.2 µm or the like. The pore diameter of the filter 13 may be set up in accordance with the size and the length of the single-walled carbon nanotubes to be dispersed in the carbon nanotube solution.

Figure 3A:
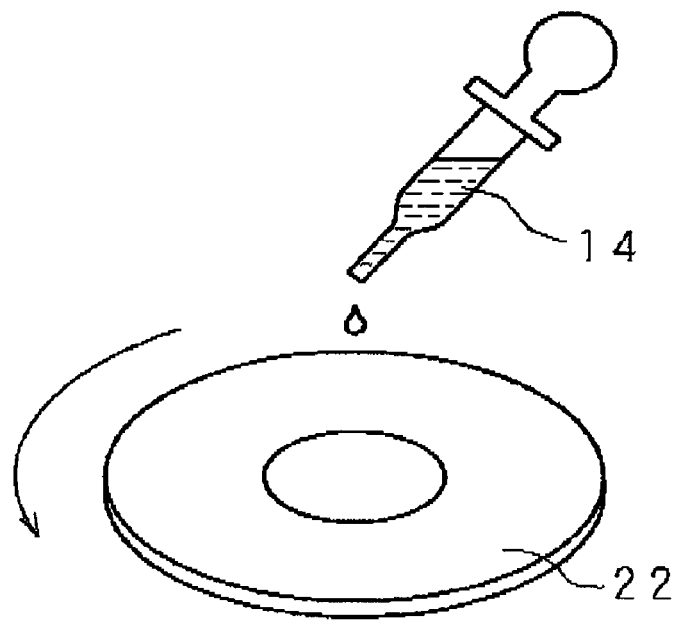
FIGS. 3A and 3B are conceptual diagrams showing a method of preparing a film sample containing single-walled carbon nanotubes.
Figure 3B:
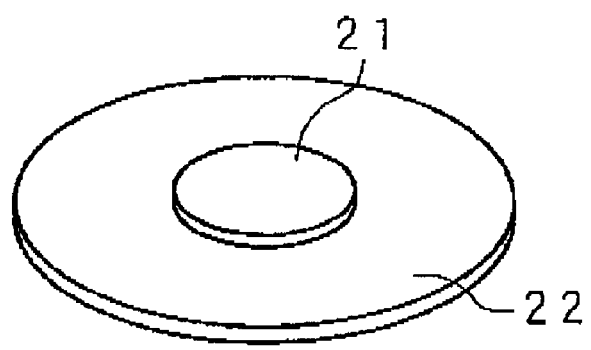

FIGS. 3A and 3B are conceptual diagrams showing a method of preparing a film sample containing single-walled carbon nanotubes. The film sample is prepared by spin coating. That is, as shown in FIG. 3A, the carbon nanotube solution 14 containing single-walled carbon nanotubes is dripped onto a revolving substrate 22. The substrate 22 is composed of a quartz substrate or the like. When the dripped carbon nanotube solution 14 spreads over the substrate 22, the water evaporates immediately. Thus, as shown in FIG. 3B, a film sample 21 is formed on the substrate 22. In the film sample 21 prepared as described here, the water serving as solvent has volatilized from the carbon nanotube solution 14. Thus, the sample is composed almost completely of single-walled carbon nanotubes and CMC. The film sample 21 is employed as the carbon nanotube-containing substance according to the present embodiment.

FIG. 4 is a schematic diagram showing the structure of a Raman spectrometer according to Embodiment 1. The Raman spectrometer serves as the degree-of-dispersion determination apparatus for single-walled carbon nanotubes according to the present embodiment. The Raman spectrometer includes a sample stage 32 as well as a laser light source 31, a half mirror 35, and an objective lens 36 that serve as a projection section. Laser light emitted from the laser light source 31 is redirected by the half mirror 35 so as to be projected through the objective lens 36 onto a sample located on the sample stage 32. In the present embodiment, the substrate 22 on which the film sample 21 has been formed is placed on the sample stage 32. That is, the laser light from the laser light source 31 is projected onto the film sample 21 formed on the surface of the substrate 22 placed on the sample stage 32. Further, in the present embodiment, the wavelength of the laser light emitted from the laser light source 31 is 633 nm. When the laser light is projected onto the film sample 21, scattered light containing Raman scattering light and Rayleigh scattering light is generated in the film sample 21. The Raman spectrometer further includes a spectroscope 33 and an optical notch filter 37. The scattered light generated in the film sample 21 passes through the objective lens 36, the half mirror 35, and the optical notch filter 37, and then enters the spectroscope 33. The optical notch filter 37 is constructed such that the notch frequency is equal to the frequency of the Rayleigh scattering light, that is, the frequency of the laser light emitted from the laser light source 31. Among the scattered light components generated in the film sample 21, the Rayleigh scattering light is removed by the optical notch filter 37, while the Raman scattering light enters the spectroscope 33.

Further, the Raman spectrometer includes a photodetector 34 composed of a CCD (Charge Coupled Device) photosensor or a photomultiplier tube (PMT). The spectroscope 33 spectrum-analyzes the entered Raman scattering light. Then, the photodetector 34 detects the Raman scattering light analyzed by the spectroscope 33. The Raman spectrometer further includes a computer 4 connected to the spectroscope 33 and the photodetector 34. The photodetector 34 inputs to the computer 4 an electric signal corresponding to the optical intensity of the detected Raman scattering light. Here, the photodetector 34 may be composed of a photosensor of another type.

Figure 5:
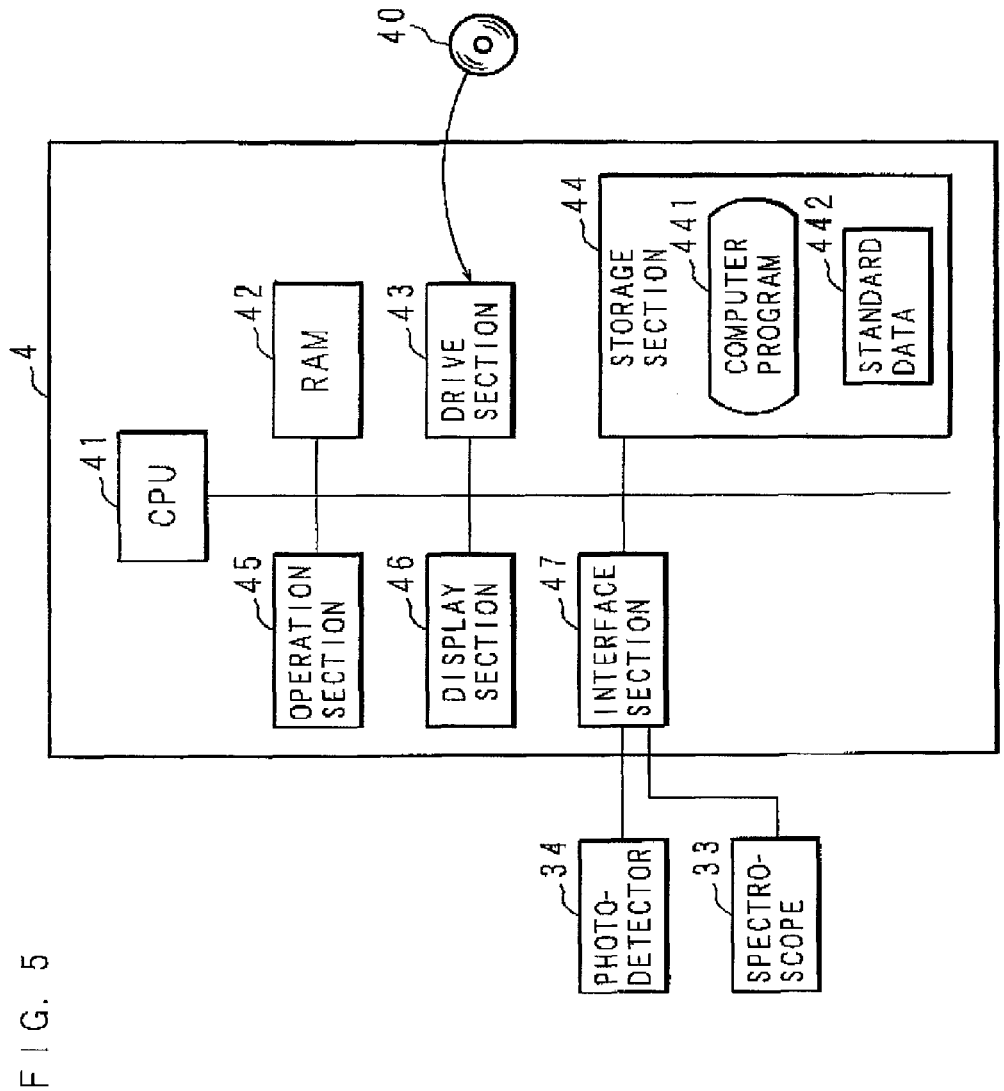
FIG. 5 is a block diagram showing an internal configuration of a computer.

FIG. 5 is a block diagram showing an internal configuration of the computer 4. The computer 4 is constructed from a general purpose computer such as a personal computer (PC). The computer 4 includes: a CPU 41 for calculation; a RAM 42 for storing temporary information generated by arithmetic operation; a drive section 43 such as a CD-ROM drive for reading information from a recording medium 40 such as an optical disk; and a storage section 44 such as a hard disk. The CPU 41 causes the drive section 43 to read a computer program 441 from the recording medium 40, and then stores the read-out computer program 441 into the storage section 44. The computer program 441 is loaded from the storage section 44 to the RAM 42 when necessary. Then, on the basis of the loaded computer program 441, the CPU 41 executes processing required by the Raman spectrometer.

Further, the computer 4 includes: an operation section 45 such as a keyboard or a pointing device through which information such as various kinds of processing instructions is inputted when a user operates it; and a display section 46 such as a liquid crystal display for displaying various kinds of information. The computer 4 further includes an interface section 47 connected to the spectroscope 33 and the photodetector 34.

The CPU 41 transmits a necessary control signal to the spectroscope 33 through the interface section 47, so as to controls the wavelength of the Raman scattering light to be extracted by the spectroscope 33 from among the entered Raman scattering light components. The photodetector 34 detects the Raman scattering light extracted by the spectroscope 33, and then inputs to the computer 4 an electric signal that indicates the optical intensity of the detected Raman scattering light. The CPU 41 receives the electric signal from the photodetector 34 through the interface section 47. The CPU 11 converts the wavelength of the Raman scattering light extracted by the spectroscope 33 into a Raman shift, and then stores the Raman shift and the optical intensity of the Raman scattering light detected by the photodetector 34, in a correspondence manner to each other into the storage section 44. With changing the wavelength of the Raman scattering light to be extracted by the spectroscope 33, the CPU 41 sequentially receives electric signals from the photodetector 34 through the interface section 47, and then stores into the storage section 44 the optical intensity of the Raman scattering light corresponding to each Raman shift. In this way, the computer 4 performs the processing of acquiring a Raman spectrum.

Figure 6A:
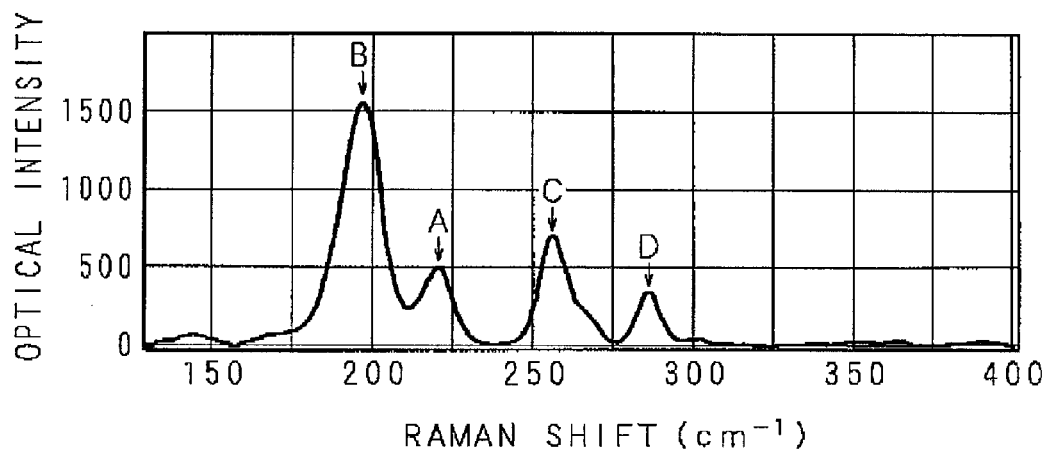
FIGS. 6A and 6B are characteristics diagrams each showing a Raman spectrum acquired by a Raman spectrometer according to an embodiment.
Figure 6B:
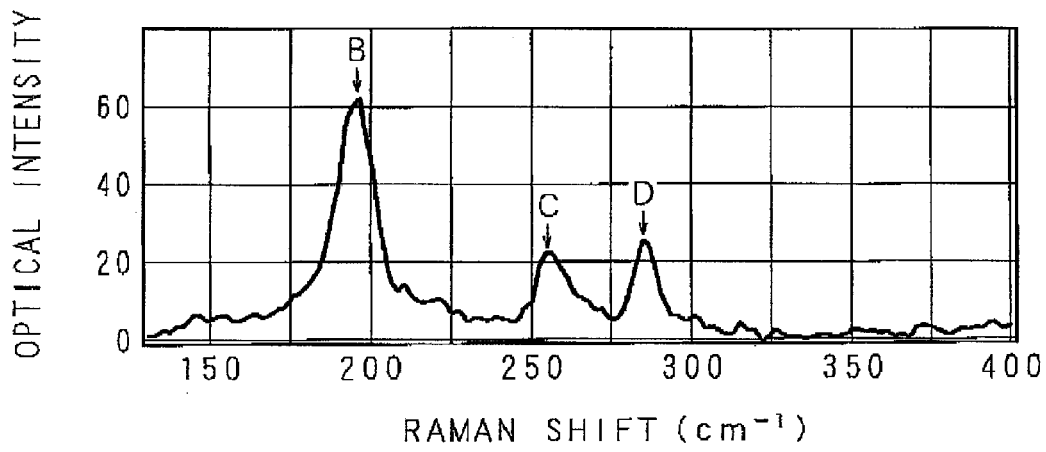

FIGS. 6A and 6B are characteristics diagrams each showing a Raman spectrum acquired by the Raman spectrometer. The Raman spectrum shown in FIG. 6 is a Raman spectrum in a case that the wavelength of the laser light projected onto the film sample 21 is 633 nm. The horizontal axis in FIG. 6 indicates the Raman shift in terms of the wave number in the unit of $cm^{-1}$. The vertical axis in FIG. 6 indicates in an arbitrary unit the optical intensity corresponding to the Raman shift at each wave number. The CPU 41 of the computer 4 performs the processing of displaying the acquired Raman spectrum on the display section 46 as shown in FIG. 6. FIG. 6A shows a Raman spectrum obtained by projecting laser light onto the film sample 21 containing aggregates of a plurality of single-walled carbon nanotubes that aggregate with each other. Further, FIG. 6B shows a Raman spectrum obtained by projecting laser light onto the film sample 21 in which isolated single-walled carbon nanotubes are dispersed.

The Raman spectrum shown in FIG. 6A has four peaks A, B, C, and D. In the Raman spectrum shown in FIG. 6A, the Raman shift of the peak A is 222 $cm^{-1}$, the Raman shift of the peak 13 is 197 $cm^{-1}$, the Raman shift of the peak C is 257 $cm^{-1}$, and the Raman shift of the peak D is 285 $cm^{-1}$. In the Raman spectrum shown in FIG. 6B, the peaks B, C, and D are observed. However, the peak A is not observed clearly. In the Raman spectrum shown in FIG. 6B, the Raman shift of the peak B is 197 $cm^{-1}$, the Raman shift of the peak C is 254 $cm^{-1}$, and the Raman shift of the peak D is 285 $cm^{-1}$.

The peaks B, C, and D contained in the Raman spectrum shown in FIG. 6 are theoretically expected as peaks to be contained in a Raman spectrum acquired from isolated single-walled carbon nanotubes. However, the peak A shown in FIG. 6A is a peak not expected theoretically. As shown in FIG. 6A, the peak A is contained in the Raman spectrum acquired from the sample containing aggregates of a plurality of single-walled carbon nanotubes that aggregate with each other. In contrast, as shown in FIG. 6E, the peak A is not contained in the Raman spectrum acquired from the sample in which isolated single-walled carbon nanotubes are dispersed. Further, the intensity of the peak A increases with increasing ratio of aggregates within the single-walled carbon nanotubes, and decreases with increasing ratio of isolated single-walled carbon nanotubes. Thus, it is inferred that the Raman scattering light corresponding to the peak A is Raman scattering light that is caused by aggregates of a plurality of single-walled carbon nanotubes that aggregate with each other and that relates to interactions between nearby carbon nanotubes. Further, the intensity of the peak A is inferred to depends on the amount of aggregates of a plurality of single-walled carbon nanotubes that aggregate with each other.

As described above, since the intensity of the peak A depends on the amount of aggregates of a plurality of single-walled carbon nanotubes that aggregate with each other, this intensity serves as an index for determining the degree of dispersion corresponding to the ratio of single-walled carbon nanotubes that do not form aggregates and are in an isolated state. That is, a smaller intensity of the peak A indicates a higher degree of dispersion, while a higher intensity of the peak A indicates a lower degree of dispersion. The intensity of each peak depends also on the overall amount of single-walled carbon nanotubes. Thus, when the intensity of the peak A is to be employed as an index for the degree of dispersion, it is sufficient that the intensity of the peak A is normalized by the intensity of another predetermined peak. In the present embodiment, the intensity of the peak A is normalized by the intensity of the peak B. For example, the intensity of the peak A is normalized by a method of dividing the intensity of the peak A with the intensity of the peak B or alternatively a method of calculating the intensity of the peak A at the time when the intensity of the peak B is brought into a predetermined value in a state that the intensity ratio between the peak A and the peak B is maintained. Here, in the present embodiment, the intensity of the peak A may be normalized relative to another peak such as the peak C and the peak D.

The Raman spectrum shown in FIG. 6 is obtained in a case that the wavelength of the laser light is 633 nm. When laser light at another wavelength is employed, a Raman spectrum different from the Raman spectrum shown in FIG. 6 is obtained. Even when laser light at another wavelength is employed, a Raman spectrum is obtained that contains peaks corresponding to the peaks B, C, and D caused by isolated single-walled carbon nanotubes and the peak A caused by aggregates of single-walled carbon nanotubes. Nevertheless, in a case that laser light at another wavelength is employed, the peak corresponding to the peak A may overlap with another peak in the Raman spectrum, and hence cannot clearly be observed. In comparison with a case that laser light at another wavelength is employed, when the wavelength of the employed laser light is 633 nm, the peak A caused by aggregates of single-walled carbon nanotubes is observed clearly and is least affected by other peaks in the measurement of the intensity. Thus, in order to obtain the peak A serving as a satisfactory index for determining the degree of dispersion, the laser light source 31 optimally need have a laser light wavelength near 633 nm.

The energy of the laser light having the wavelength of 633 nm is approximately 1.9 eV. Equivalent resonance phenomenon is obtained within a range of 0.1 eV in the excitation-light energy width. Thus, in the present embodiment, it is sufficient that the energy of the laser light emitted from the laser light source 31 falls within the range of 1.9±0.1 eV. This energy of the laser light corresponds to the wavelength of 620 nm to 690 nm. The Raman shift of the peak A serving as a satisfactory index for determining the degree of dispersion is 221±5 $cm^{-1}$. This value of ±5 $cm^{-1}$ corresponds to the measurement error in the Raman spectrometer. Similarly, the Raman shift of the peak B is 197±5 $cm^{-1}$.

The storage section 44 of the computer 4 stores the standard data 442 used for comparing with a normalized intensity of the peak A so as to determine the degree of dispersion of single-walled carbon nanotubes. The standard data 442 records the intensity of the peak A measured and normalized in advance by using a standard sample in which the degree of dispersion of single-walled carbon nanotubes is adjusted into a particular value. For example, the degree of dispersion of single-walled carbon nanotubes is defined as the ratio of single-walled carbon nanotubes isolated in the carbon nanotube-containing substance or alternatively the optical intensity of photoluminescence emitted from a carbon nanotube-containing substance that contains a predetermined amount of single-walled carbon nanotubes. In the standard data 442, each particular value of degree of dispersion and each particular value of normalized intensity of the peak A are recorded in a correspondence manner to each other.

Figure 7:
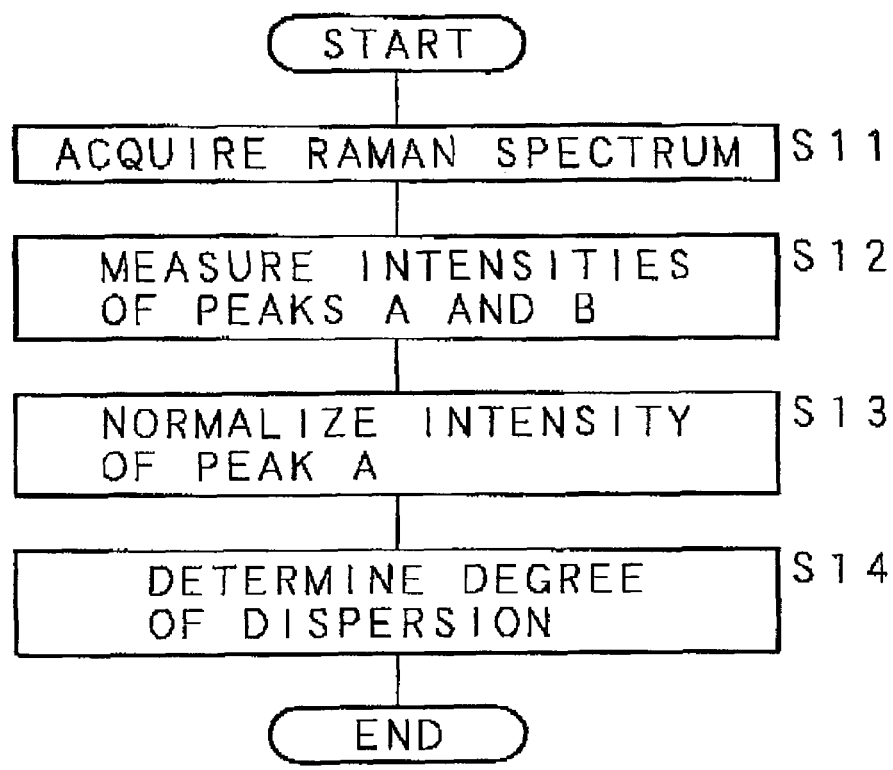
FIG. 7 is a flow chart showing a procedure of processing that a Raman spectrometer according to Embodiment 1 determines the degree of dispersion of single-walled carbon nanotubes in a film sample.

FIG. 7 is a flow chart showing a procedure of processing that the Raman spectrometer according to Embodiment 1 determines the degree of dispersion of single-walled carbon nanotubes in the film sample 21. The laser light source 31 projects laser light at a wavelength of 633 nm onto the film sample 21. The spectroscope 34 extracts Raman scattering light at each wavelength from the scattered light obtained from the film sample 21. The photodetector 34 detects the Raman scattering light at each wavelength, and then inputs to the computer 4 an electric signal corresponding to the detected Raman scattering light. As a result of the above-mentioned processes, the Raman spectrometer acquires a Raman spectrum (S11). Then, from the acquired Raman spectrum, the CPU 41 of the computer 4 measures the intensity of the peak A at Raman shift 221±5 $cm^{-1}$ and the intensity of the peak B at Raman shift 197±5 $cm^{-1}$ (S12). At step S12, from the Raman spectrum, the CPU 41 acquires the value of the maximum optical intensity among the optical intensities corresponding to the Raman shift range of 221±5 $cm^{-1}$, so as to measure the intensity of the peak A. Further, the CPU 41 may acquire from the Raman spectrum the value of optical intensity corresponding to a Raman shift such as 221 $cm^{-1}$ defined in advance within a range of 221±5 $cm^{-1}$, so as to measure the intensity of the peak A. Further, no peak other than the peak A is included within the Raman shift range of 210 to 230 $cm^{-1}$. Thus, the intensity of the peak A may be acquired in the Raman shift range of 210 to 230 $cm^{-1}$. That is, the CPU 41 may acquire from the Raman spectrum, the value of the maximum optical intensity among the optical intensities within the Raman shift range of 210 to 230 $cm^{-1}$, so as to measure the intensity of the peak A. Further, the CPU 41 may acquire from the Raman spectrum the value of optical intensity corresponding to a predetermined Raman shift within the range of 210 to 230 $cm^{-1}$, so as to measure the intensity of the peak A. The CPU 41 may measure the intensity of the peak B by a similar method.

Then, the CPU 41 divides the measured intensity of the peak A with the intensity of the peak B so as to normalize the intensity of the peak A (S13). Then, the CPU 41 compares the value of the normalized intensity of the peak A with that in the standard data 442 stored in the storage section 44, so as to determine the degree of dispersion of single-walled carbon nanotubes contained in the film sample 21 (S14). At step S14, from among the intensity values of the peak A recorded in the standard data 442, the CPU 41 selects a value closest to the normalized intensity of the peak A obtained at step S13. Then, the CPU 41 determines that the value of the degree of dispersion corresponding to the selected value is the value of the degree of dispersion of single-walled carbon nanotubes. Alternatively, on an extrapolation curve obtained by extrapolating the relation between the degree of dispersion and the normalized intensity of the peak A recorded in the standard data 442, the CPU 41 may acquire a value of the degree of dispersion corresponding to the normalized intensity of the peak A obtained at step S13, and then determine that the calculated value is the value of the degree of dispersion of single-walled carbon nanotubes. Further, the CPU 41 may perform the processing of determining that the degree of dispersion of single-walled carbon nanotubes falls within a particular value range, like the processing that when the normalized intensity of the peak A obtained at step S13 is at or below the value of the intensity of the peak A corresponding to a degree of dispersion x, it is determined that the degree of dispersion is greater than or equal to x. Then, the CPU 41 performs the processing of storing the determination result of the degree of dispersion into the storage section 44 or alternatively displaying the determination result onto the display section 46, and then terminates the processing.

In the present embodiment, a Raman spectrum is acquired by projecting laser light of 1.9±0.1 eV onto a carbon nanotube-containing substance. Then, On the basis of the intensity of the peak at Raman shift 221±5 $cm^{-1}$ caused by aggregates of single-walled carbon nanotubes, the degree of dispersion of the single-walled carbon nanotubes is determined. As such, when the intensity of a particular peak contained in a Raman spectrum is measured, the degree of dispersion is determined. Thus, the degree of dispersion of single-walled carbon nanotubes in a carbon nanotube-containing substance can be evaluated easily and clearly.

Here, the present embodiment has been described for a case that Raman scattering light is measured for the film sample 21 prepared by the method described with reference to FIGS. 2 and 3 so that the degree of dispersion of single-walled carbon nanotubes is determined. However, the method of preparing a carbon nanotube-containing substance is not limited to this method. In the present embodiment, a carbon nanotube-containing substance prepared by a method different from the method described in the present embodiment may be employed, and then Raman scattering light may similarly be measured so that the degree of dispersion of single-walled carbon nanotubes may be determined. Further, the carbon nanotube-containing substance need not be in the form of a thin film and may be in another form. For example, the carbon nanotube-containing substance may be in the form of solution.

Further, the present embodiment has been described for a case that a computer 4 provided in a Raman spectrometer performs the processing of determining the degree of dispersion. However, the present embodiment is not hunted to this configuration. That is, acquisition of a Raman spectrum and determination of the degree of dispersion may be performed by separate apparatuses. For example, the Raman spectrometer may perform up to the acquisition of a Raman spectrum. Then, the data of the acquired Raman spectrum may be read by another computer, and then another computer performs the processing of determining the degree of dispersion on the basis of the read-out Raman spectrum.

Embodiment 2

FIG. 8 is a schematic diagram showing the structure of a Raman spectrometer according to Embodiment 2. The Raman spectrometer according to the present embodiment does not include a spectroscope, and includes an optical band pass filter 38. The optical band pass filter 38 allows transmission of Raman scattering light at Raman shift $221\pm5$ cm$^{-1}$ generated by laser light of $1.9\pm0.1$ eV, and cuts off light at other wavelengths. Further, in the Raman spectrometer, scattered light generated in the film sample 21 passes through the objective lens 36, the half mirror 35, the optical notch filter 37, and the optical band pass filter 38, and then enters the photodetector 34. The other points in the configuration of the Raman spectrometer are similar to those of Embodiment 1 shown in FIG. 4. Thus, like parts are designated by like numerals, and their description is omitted. Among the scattered light components generated by the laser light of $1.9\pm0.1$ eV projected from the laser light source 31 onto the film sample 21, Rayleigh scattering light is removed by the optical notch filter 37. Thus, Raman scattering light at Raman shift $221\pm5$ cm$^{-1}$ alone passes through the optical band pass filter 38, and then is detected by the photodetector 34.

The internal configuration of the computer 4 is similar to that of Embodiment 1 shown in FIG. 5. Thus, description is omitted. The standard data 442 stored in the storage section 44 of the computer 4 records the intensity of Raman scattering light measured in advance by using a standard sample in which the degree of dispersion of single-walled carbon nanotubes is adjusted into a particular value. The intensity of Raman scattering light recorded in the standard data 442 is the intensity of Raman scattering light at Raman shift $221\pm5$ cm$^{-1}$ generated when laser light of $1.9\pm0.1$ eV is projected onto a standard sample in the same apparatus or in an apparatus having the same optical design. In the standard data 442, each particular value of degree of dispersion and each particular value of intensity of Raman scattering light are recorded in a correspondence manner to each other.

Figure 9:
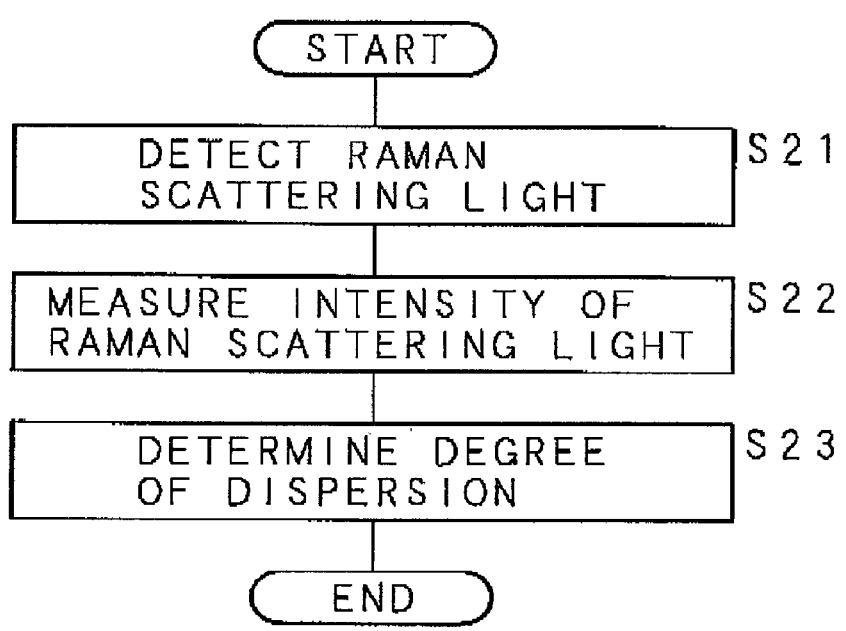
FIG. 9 is a flow chart showing a procedure of processing that a Raman spectrometer according to Embodiment 2 determines the degree of dispersion of single-walled carbon nanotubes in a film sample.

FIG. 9 is a flow chart showing a procedure of processing that the Raman spectrometer according to Embodiment 2 determines the degree of dispersion of single-walled carbon nanotubes in the film sample 21. The laser light source 31 projects laser light of $1.9\pm0.1$ eV (having a wavelength of approximately 633 nm) onto the film sample 21. Then, generated Raman scattering light at Raman shift $221\pm5$ cm$^{-1}$ is detected by the photodetector 34 (S21). The photodetector 43 inputs to the computer 4 an electric signal corresponding to the optical intensity of the detected Raman scattering light. Then, the CPU 41 of the computer 4 measures the intensity of the detected Raman scattering light on the basis of the inputted electric signal (S22).

Then, the CPU 41 compares the measured intensity of the Raman scattering light with that in the standard data 442 stored in the storage section 44, so as to determine the degree of dispersion of single-walled carbon nanotubes contained in the film sample 21 (S23). At step S23, it is sufficient that the CPU 41 performs processing similar to step S14 in Embodiment 1. Then, the CPU 41 performs the processing of storing the determination result of the degree of dispersion into the storage section 44 or alternatively displaying the determination result onto the display section 46, and then terminates the processing.

Also in the present embodiment, the degree of dispersion of single-walled carbon nanotubes in a carbon nanotube-containing substance can be evaluated easily and clearly. In the present embodiment, the Raman spectrometer need not include a spectroscope. This permits size reduction in the degree-of-dispersion determination apparatus for single-walled carbon nanotubes according to the present embodiment. Further, a Raman spectrum need not be acquired. This reduces the time necessary in determining the degree of dispersion.

Embodiment 3

As described above, isolated single-walled carbon nanotubes have the property of generating photoluminescence. The emission wavelength of the photoluminescence depends on the diameter of the single-walled carbon nanotube. Thus, in order that a luminescence material for generating photoluminescence of a specified wavelength should be prepared, a carbon nanotube-containing substance that contains single-walled carbon nanotubes having a particular diameter need be prepared. Meanwhile, the Raman scattering light at Raman shift $221\pm5$ cm$^{-1}$ generated by the laser light of $1.9\pm0.1$ eV is observed by single-walled carbon nanotubes having a diameter of approximately 0.9 nm. When the diameter of the single-walled carbon nanotube is adjusted for the purpose of adjustment of the wavelength of photoluminescence, a situation can arise that single-walled carbon nanotubes having a diameter of approximately 0.9 nm are contained only by a small amount in the carbon nanotube-containing substance. At that time, the above-mentioned Raman scattering light serving as an index for determining the degree of dispersion cannot be observed, and hence the degree of dispersion of single-walled carbon nanotubes in the carbon nanotube-containing substance cannot be determined.

Figure 10:
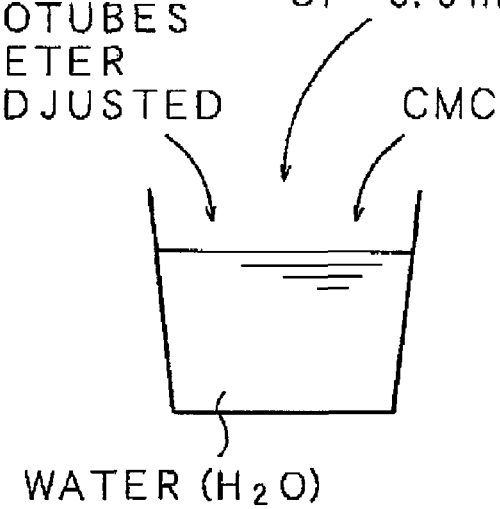
FIG. 10 is a conceptual diagram showing an example of a method of preparing a carbon nanotube-containing substance according to Embodiment 3.

In Embodiment 3, in preparing the carbon nanotube-containing substance, single-walled carbon nanotubes having a diameter of approximately 0.9 nm are mixed in. FIG. 10 is a conceptual diagram showing an example of the method of preparing a carbon nanotube-containing substance according to Embodiment 3. Carboxymethylcellulose (CMC) and single-walled carbon nanotubes whose diameter has been adjusted for the purpose of adjustment of the wavelength of photoluminescence are supplied into water (H2O) serving as solvent. Further, single-walled carbon nanotubes having a diameter of approximately 0.9 nm axe supplied. Then, mixing and stirring are performed so that solution containing carbon nanotubes is prepared. The amount of supply of the single-walled carbon nanotubes having a diameter of approximately 0.9 nm is adjusted in accordance with the desired optical intensity of the photoluminescence generated by the single-walled carbon nanotubes having a diameter of approximately 0.9 nm. For example, when the optical intensity of the photoluminescence generated by the single-walled carbon nanotubes having a diameter of approximately 0.9 nm need be suppressed, the amount of supply is reduced. Further, for example, when the light emission of the photoluminescence generated by the single-walled carbon nanotubes having a diameter of approximately 0.9 nm is permitted, the amount of supply is increased.

By using solution prepared as shown in FIG. 10, a carbon nanotube-containing substance is prepared by a method similar to that of Embodiment 1. In the prepared carbon nanotube-containing substance, a part of single-walled carbon nanotubes having a diameter of approximately 0.9 nm aggregate with single-walled carbon nanotubes of other kinds so as to form aggregates. When laser light of 1.9±0.1 eV is projected onto the single-walled carbon nanotubes prepared in this way so that a Raman spectrum is acquired, a Raman spectrum is obtained that includes the individual peaks shown in FIG. 6. With receiving interactions from other single-walled carbon nanotubes in the aggregate, the single-walled carbon nanotube having a diameter of approximately 0.9 nm generates Raman scattering light corresponding to a Raman shift of $221 \pm 5 \, cm^{-1}$. By using the prepared carbon nanotube-containing substance, the determination method for the degree of dispersion described in Embodiment 1 or 2 is executed so that the degree of dispersion of the single-walled carbon nanotubes in the carbon nanotube-containing substance is determined.

In the present embodiment, single-walled carbon nanotubes having a diameter of approximately 0.9 nm are mixed into a carbon nanotube-containing substance. This permits determination of the degree of dispersion of single-walled carbon nanotubes in the carbon nanotube-containing substance. Thus, even when a carbon nanotube-containing substance is employed that contains mainly carbon nano-tubes not generating Raman scattering light serving as an index for determining the degree of dispersion, the degree of dispersion of single-walled carbon nanotubes can be determined according to the present embodiment. Accordingly, in the present embodiment, the degree of dispersion of single-walled carbon nanotubes can be evaluated clearly for a carbon nanotube-containing substance that contains carbon nanotubes of an arbitrary kind.

Embodiment 4

Figure 11:
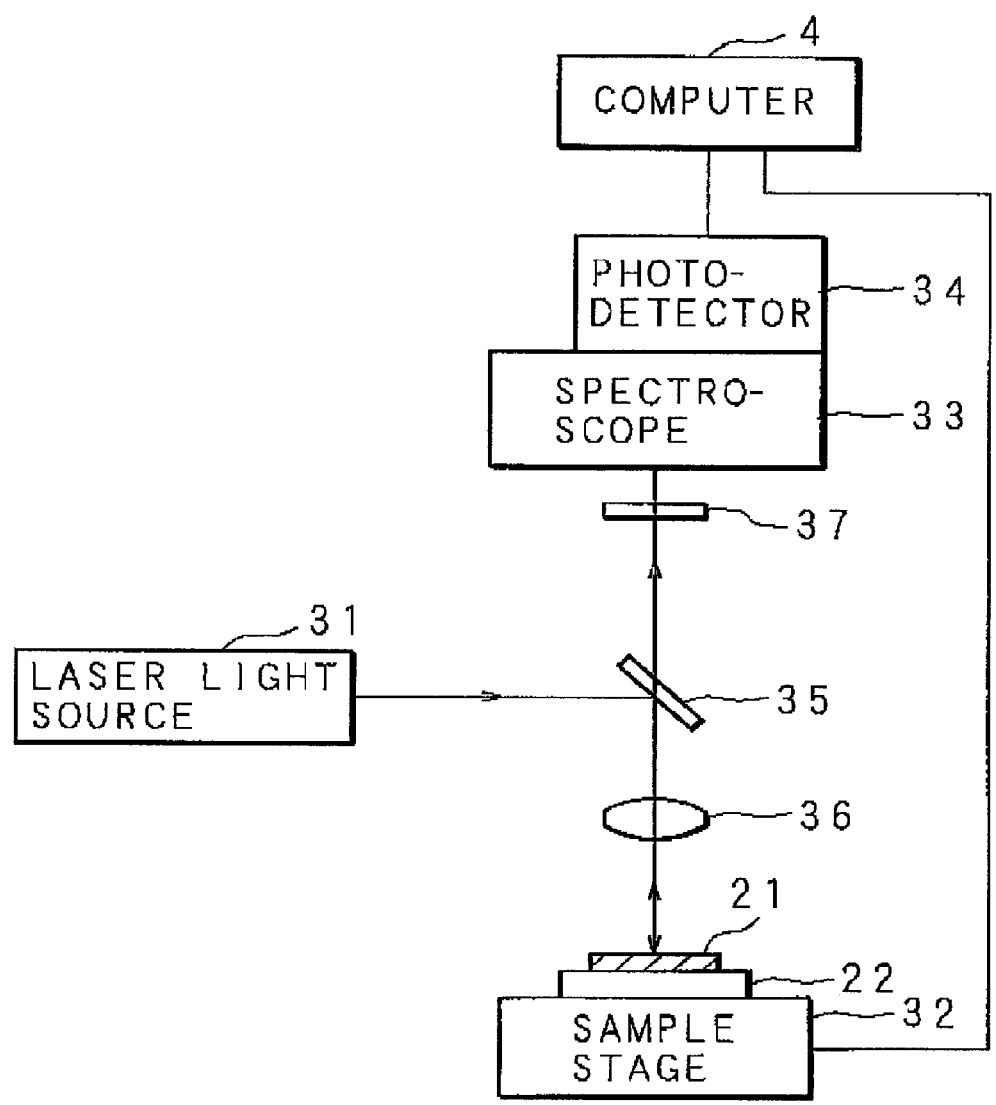
FIG. 11 is a schematic diagram showing a structure of a Raman spectrometer according to Embodiment 4.

In Embodiment 4, the distribution of the degree of dispersion of single-walled carbon nanotubes is acquired in the film sample 21 composed of a carbon nanotube-containing substance. FIG. 11 is a schematic diagram showing the structure of a Raman spectrometer according to Embodiment 4. In the Raman spectrometer according to the present embodiment, the optical diameter of laser light from the laser light source 31 is reduced into 1 μm or the like by the objective lens 36. The Raman spectrometer according to the present embodiment includes the sample stage 32 and a drive mechanism (not shown) that serve as a drive section. By virtue of the drive mechanism (not shown), the sample stage 32 can move the sample in two orthogonal directions crossed to the optical axis of laser light. The internal configuration of the computer 4 is similar to that of Embodiment 1 shown in FIG. 5. The sample stage 32 is connected to the interface section 47 of the computer 4. The computer 4 performs the processing of transmitting to the sample stage 32 a control signal for causing the sample stage 32 to move the sample. Then, in accordance with the control signal from the computer 4, the sample stage 32 moves the sample. In the Raman spectrometer according to the present embodiment, the sample stage 32 moves the substrate 22 and the film sample 21 in accordance with a control signal from the computer 4, so that the part onto which laser light is projected can be moved on, the film sample 21. The other points in the configuration of the Raman spectrometer are similar to those of Embodiment 1 shown in FIG. 4. Thus, like parts are designated by like numerals, and their description is omitted. Alternatively, the sample stage 32 may be fixed while the laser light projection side may be moved. In this case, the drive mechanism moves the half mirror 35 and the objective lens 36.

Figure 12:
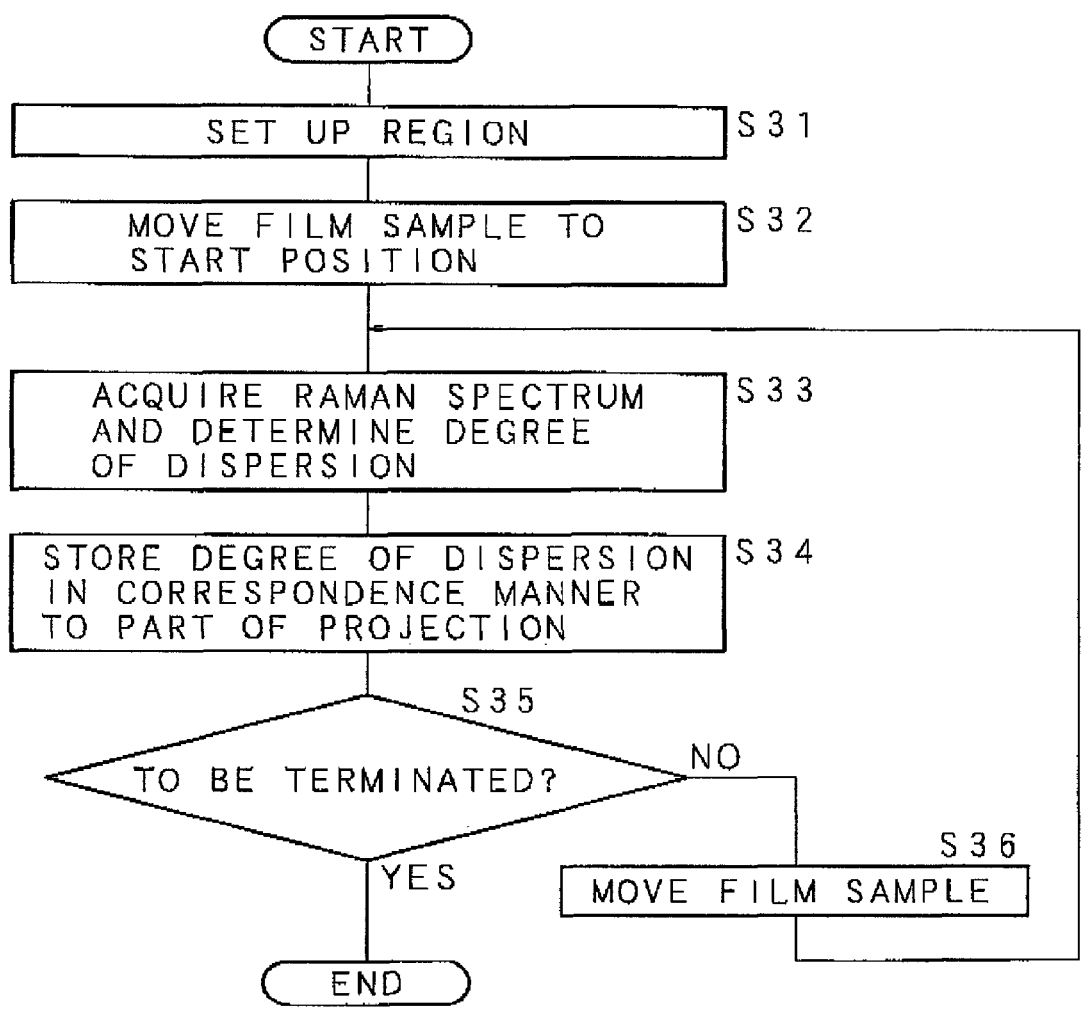
FIG. 12 is a flow chart showing a procedure of processing that a Raman spectrometer according to Embodiment 4 measures the distribution of the degree of dispersion of single-walled carbon nanotubes in a film sample.

FIG. 12 is a flow chart showing a procedure of processing that the Raman spectrometer according to Embodiment 4 measures the distribution of the degree of dispersion of single-walled carbon nanotubes in the film sample 21. In accordance with an instruction inputted when a user operates the operation section 45, the CPU 41 of the computer 4 sets up a region where the distribution of the degree of dispersion is to be acquired on the film sample 21 (S31). The CPU 41 transmits a predetermined control signal through the interface section 47 to the sample stage 32. Then, in accordance with the control signal, the sample stage 32 moves the film sample 21 such that the part where the degree of dispersion is to be determined at first within the set-up region should be located at the position onto which laser light is projected (S32). In the Raman spectrometer, laser light is projected from the laser light source 31 onto the film sample 21, and the processing similar to that at steps S11 to S14 shown in the flow chart of FIG. 7 are performed. As a result, acquisition of a Raman spectrum at the part onto which laser light is projected on the film sample 21 is acquired, and the degree of dispersion of single-walled carbon nanotubes is determined (S33).

Then, the CPU 41 stores into the storage section 44 the determined degree of dispersion of single-walled carbon nanotubes in a correspondence manner to the information that indicates the position of laser light projection (S34) Then, the CPU 41 determines whether the entirety of determination of the degree of dispersion within the set-up region has been completed (S35). When determination of the degree of dispersion is not yet completed within the set-up region (S35: NO), The CPU 41 transmits a predetermined control signal through the interface section 47 to the sample stage 32. Then, in accordance with the control signal, the sample stage 32 moves the film sample 21 such that the part where the degree of dispersion is to be determined next within the set-up region should be located at the position onto which laser light is projected (S36). Then, the Raman spectrometer returns the processing to step S33, and then performs acquisition of a Raman spectrum and determination of the degree of dispersion, in the next part. At step S35, when determination of the degree of dispersion has been completed within the set-up region (S35: YES), the Raman spectrometer terminates the processing.

In the above-mentioned processing, when the degree of dispersion of single-walled carbon nanotubes in each part on the film sample 21 is stored into the storage section 44, the Raman spectrometer acquires the distribution of the degree of dispersion of single-walled carbon nanotubes on the film sample 21. For example, the CPU 41 may perform the processing of visualizing the distribution of the degree of dispersion, like the processing that an image in which each part and the degree of dispersion on the film sample 21 are made in correspondence to each other is generated and displayed on the display section 46.

In the present embodiment, each part on the film sample 21 containing single-walled carbon nanotubes and the degree of dispersion in each part are made in correspondence to each other, so that the distribution of the degree of dispersion of single-walled carbon nanotubes on the film sample 21 is acquired. The distribution of the degree of dispersion of single-walled carbon nanotubes corresponds to the emission distribution of photoluminescence. Thus, when the distribution of the degree of dispersion of single-walled carbon nanotubes in a carbon nanotube-containing substance is obtained, the quality of the carbon nanotube-containing substance as a luminescence material can be evaluated.

Here, the present embodiment has been described for a case that the film sample 21 was employed as a measurement object. However, the present embodiment is not limited to this situation. That is, as long as its shape contains a planar part, the carbon nanotube-containing substance adopted as a measurement object may have another shape. For example, the carbon nanotube-containing substance serving as a measurement object may be prepared by cutting out and surface-polishing of a block carbon nanotube-containing substance. Further, the present embodiment has been described for a case that determination of a Raman spectrum and determination of the degree of dispersion are performed at one part of a carbon nanotube-containing substance and then this processing is repeated in individual parts. However, the present embodiment is not limited to this approach. In the present embodiment, the distribution of the Raman spectrum may acquired once with moving the position of laser light projection. Then, the distribution of the degree of dispersion may be acquired from the acquired distribution of the Raman spectrum. Further, the present embodiment has been described for a case that in the Raman spectrometer, the sample is moved by the sample stage 32. However, the present embodiment is not limited to this configuration. That is, the optical axis of laser light may be moved so that the part onto which laser light is projected may be moved on the sample.

Further, the present embodiment has been described for a case that the distribution of the degree of dispersion of single-walled carbon nanotubes is acquired in the film sample 21. However, the present embodiment is not limited to this situation. In the present embodiment, the average value of the degree of dispersion of single-walled, carbon nanotubes may be acquired in the film sample 21. In this case, with moving the position of laser light projection, the Raman spectrometer acquires Raman spectra at a plurality of measurement points, then calculates the average of a plurality of acquired Raman spectra, and then determines the degree of dispersion of single-walled carbon nanotubes on the basis of the calculated average Raman spectrum. As a result of this processing, the average value of the degree of dispersion of single-walled carbon nanotubes in the film sample 21 is obtained. This improves the reliability and the reproducibility in the determined value of the degree of dispersion.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention(s) has (have) been described in detail, it should be understood that the various changes, substitutions, and alterations could be made hereto without departing from the spirit and scope of the invention.

What is claimed is:

1. A method of determining a degree of dispersion corresponding to a ratio of single-walled carbon nanotubes that do not form aggregates and are in an isolated state within single-walled carbon nanotubes contained in a carbon nanotube-containing substance, comprising:

detecting Raman scattering light generated by projecting monochromatic light into a carbon nanotube-containing substance;

measuring an intensity of the Raman scattering light corresponding to a predetermined Raman shift corresponding to said monochromatic light; and on the basis of the measured intensity of the Raman scattering light, determining a degree of dispersion of the single-walled carbon nanotubes in said carbon nanotube-containing substance, wherein an energy of the monochromatic light projected into said carbon nanotube-containing substance is 1.9±0.1 eV, and said predetermined Raman shift is 210 to 230 $cm^{-1}$ in the wave number unit.

2. The degree-of-dispersion determination method according to claim 1, wherein a Raman spectrum is acquired by detecting Raman scattering light corresponding to a plurality of Raman shifts, and an intensity is measured that is obtained by normalizing an intensity of a peak corresponding to said predetermined Raman shift contained in the acquired Raman spectrum with an intensity of a peak corresponding to a particular Raman shift.

3. The degree-of-dispersion determination method according to claim 1, wherein in preparing said carbon nanotube-containing substance, single-walled carbon nanotubes having a size causing the Raman scattering light corresponding to said predetermined Raman shift are mixed into the carbon nanotubes contained in said carbon nanotube-containing substance.

4. The degree-of-dispersion determination method according to claim 1, wherein:

said carbon nanotube-containing substance is a solid material formed in a shape having a planar part;

said monochromatic light has a beam shape;

a part onto which said monochromatic light is to be projected is moved within the planar part of said carbon nanotube-containing substance; and on the basis of the detected Raman scattering light, by determining the degree of dispersion of the single-walled carbon nanotubes distribution of the degree of dispersion of the single-walled carbon nanotubes in said carbon nanotube-containing substance is acquired.

5. An apparatus for determining a degree of dispersion corresponding to a ratio of single-walled carbon nanotubes that do not form aggregates and are in an isolated state within single-walled carbon nanotubes contained in a carbon nanotube-containing substance, comprising:

a detector for detecting Raman scattering light generated by projecting monochromatic light into a carbon nanotube-containing substance; and a processor for executing the processing of:

measuring an intensity of the Raman scattering light corresponding to a predetermined Raman shift corresponding to said monochromatic light; and on the basis of the measured intensity of the Raman scattering light, determining a degree of dispersion of the single-walled carbon nanotubes in said carbon nanotube-containing substance, wherein an energy of the monochromatic light projected into said carbon nanotube-containing substance is 1.9±0.1 eV, and said predetermined Raman shift is 210 to 230 $cm^{-1}$ in the wave number unit.

6. An apparatus for determining a degree of dispersion corresponding to a ratio of single-walled carbon nanotubes that do not form aggregates and are in an isolated state within single-walled carbon nanotubes contained in a carbon nanotube-containing substance, comprising:
- means for detecting Raman scattering light generated by projecting monochromatic light into a carbon nanotube-containing substance;
- means for measuring an intensity of the Raman scattering light corresponding to a predetermined Raman shift corresponding to said monochromatic light; and
- means for on the basis of the measured intensity of the Raman scattering light, determining a degree of dispersion of the single-walled carbon nanotubes in said carbon nanotube-containing substance, wherein
- an energy of the monochromatic light projected into said carbon nanotube-containing substance is 1.9±0.1 eV, and
- said predetermined Raman shift is 210 to 230 cm$^{-1}$ in the wave number unit.

7. An apparatus for determining a degree of dispersion corresponding to a ratio of single-walled carbon nanotubes that do not form aggregates and are in an isolated state within single-walled carbon nanotubes contained in a carbon nanotube-containing substance, comprising:
- a projection section for projecting beam-shaped monochromatic light onto a carbon nanotube-containing substance formed in a shape containing a planar part;
- a drive section for moving a part onto which said monochromatic light is to be projected, within the planar part of said carbon nanotube-containing substance;
- a detector for detecting Raman scattering light in a state that a part onto which said monochromatic light is to be projected is moved; and
- a processor for executing the processing of:
  - measuring an intensity of the Raman scattering light corresponding to a predetermined Raman shift corresponding to said monochromatic light;
  - on the basis of the measured intensity of the Raman scattering light, determining a degree of dispersion of the single-walled carbon nanotubes in said carbon nanotube-containing substance; and
  - acquiring distribution of the degree of dispersion of the single-walled carbon nanotubes in said carbon nanotube-containing substance by establishing relation between each part onto which said monochromatic light has been projected and the degree of dispersion of single-walled carbon nanotubes determined on the basis of the Raman scattering light at each part, wherein
- an energy of the monochromatic light projected into said carbon nanotube-containing substance is 1.9±0.1 eV, and
- said predetermined Raman shift is 210 to 230 cm$^{-1}$ in the wave number unit.

8. An apparatus for determining a degree of dispersion corresponding to a ratio of single-walled carbon nanotubes that do not form aggregates and are in an isolated state within single-walled carbon nanotubes contained in a carbon nanotube-containing substance, comprising:
- means for projecting beam-shaped monochromatic light onto a carbon nanotube-containing substance formed in a shape containing a planar part;
- means for moving a part onto which said monochromatic light is to be projected, within the planar part of said carbon nanotube-containing substance;
- means for detecting Raman scattering light in a state that a part onto which said monochromatic light is to be projected is moved;
- means for measuring an intensity of the Raman scattering light corresponding to a predetermined Raman shift corresponding to said monochromatic light;
- means for, on the basis of the measured intensity of the Raman scattering light, determining a degree of dispersion of the single-walled carbon nanotubes in said carbon nanotube-containing substance; and
- means for acquiring distribution of the degree of dispersion of the single-walled carbon nanotubes in said carbon nanotube-containing substance by establishing relation between each part onto which said monochromatic light has been projected and the degree of dispersion of single-walled carbon nanotubes determined on the basis of the Raman scattering light at each part is established, wherein
- an energy of the monochromatic light projected into said carbon nanotube-containing substance is 1.9±0.1 eV, and
- said predetermined Raman shift is 210 to 230 cm$^{-1}$ in the wave number unit.

* * * * *